United States Patent
Kovacevic

(10) Patent No.: US 10,675,172 B2
(45) Date of Patent: Jun. 9, 2020

(54) SPINAL THERAPY DEVICE, SYSTEM AND METHOD OF USE

(71) Applicant: Krsto Kovacevic, Pleasant Prairie, WI (US)

(72) Inventor: Krsto Kovacevic, Pleasant Prairie, WI (US)

(*) Notice: Subject to any disclaimer, the term of this patent is extended or adjusted under 35 U.S.C. 154(b) by 594 days.

(21) Appl. No.: 15/331,541

(22) Filed: Oct. 21, 2016

(65) Prior Publication Data

US 2018/0085245 A1 Mar. 29, 2018

Related U.S. Application Data

(60) Provisional application No. 62/398,687, filed on Sep. 23, 2016.

(51) Int. Cl.
*A61F 5/042* (2006.01)
*A61H 1/02* (2006.01)
*A61F 5/37* (2006.01)

(52) U.S. Cl.
CPC ........... *A61F 5/042* (2013.01); *A61F 5/3707* (2013.01); *A61H 1/0292* (2013.01); *A61H 2201/0123* (2013.01); *A61H 2201/0192* (2013.01); *A61H 2201/1607* (2013.01); *A61H 2201/1652* (2013.01)

(58) Field of Classification Search
CPC .......... A61F 5/042; A61F 5/3707; A61F 5/04; A61F 5/048; A61F 5/05883; A61F 5/37; A61H 1/0292; A61H 1/0296; A61H 1/0218; A61H 1/0222; A61H 2201/0123; A61H 2201/0192; A61H 2201/1607; A61H 2201/1652; A61H 2203/0493; A61H 2203/0481; A61H 2203/0487; A47G 25/06; A47G 25/0614; A63B 23/025

USPC .............................................. 602/36
See application file for complete search history.

(56) References Cited

U.S. PATENT DOCUMENTS

| | | | | |
|---|---|---|---|---|
| 1,535,133 A | * | 4/1925 | Richards ................ | A47H 1/022 211/104 |
| 2,285,494 A | * | 6/1942 | Cole .................... | A61H 1/0218 602/36 |
| 3,221,735 A | * | 12/1965 | Goodman ................ | A61H 1/00 602/33 |
| 4,419,990 A | * | 12/1983 | Forster ................ | A61H 1/0218 482/144 |

(Continued)

OTHER PUBLICATIONS

Drive Medical, "Over Door Traction Set," Aug. 25, 2016, http://www.drivemedical.com/index.php/cervical-traction-set-134.html. Accessed on Feb. 14, 2019. Earliest available date Aug. 25, 2016 from Wayback Machine. (Year: 2016).*

*Primary Examiner* — Alireza Nia
*Assistant Examiner* — Sophia T Chang
(74) *Attorney, Agent, or Firm* — Ceres Patent & Technology LLC; Mandy T. Garrels

(57) ABSTRACT

The inventive solution is directed to a device, system and method of use for spinal therapy by way of a bracket and strap system that allows a user to self-administer spinal decompression exercises. The bracket and strap elements of the inventive device and system are collapsible, portable. The inventive device in assembled form and in use is hooked over top a vertical door or wall panel and leveraged against the user's head where the user is in seated position below. By method of using this invention, the user's upper spinal column is extended and decompressed.

2 Claims, 7 Drawing Sheets

(56) References Cited

U.S. PATENT DOCUMENTS

2004/0084053 A1* 5/2004 Hess .................. A61F 5/055
          128/870

* cited by examiner

SPINAL THERAPY DEVICE, SYSTEM AND METHOD OF USE

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

CROSS REFERENCE TO RELATED APPLICATIONS

This nonprovisional patent application incorporates by reference in full its prior filed provisional Patent Application No. 62/398,687, and claiming priority to that earlier provisional filing date, Sep. 23, 2016, according to 35 USC 119(e).

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark office, patent file or records, but otherwise reserves all copyright rights whatsoever.

BACKGROUND OF THE INVENTION

Field of the Invention

The disclosed invention herein pertains to a spinal therapy device, system and method of use, particularly for self-administering spinal decompression treatment.

Background

Pain and injury related to spinal column alignment is a very common ailment with physiological root. Misalignment of the spinal column may lead to muscular damage and eventual skeletal bone damage from disproportionate wear. These issues may occur unnaturally from impact to the body or alternatively, from poor body posture. Spinal related pain and injury may also be caused by the impact of age and the body's physiological traits. In a single day, a person's body weight causes downward compression against the spinal column, resulting in compaction of each disc against another, stressing the muscles and nervous system there between. For those with a history of spinal injury, this type of daily compaction against the spinal column impinges on the related nervous system resulting in loss of feel or extreme pain. For individuals at any phase of suffering, decompression of the spinal cord is a necessary therapeutic treatment.

Prior art in this industry provides a variety of methods and devices for the treatment of spinal compression. Some devices require handling assistance from additional individuals while other devices aim at self-treatment and individual use. Within the realm of self-treating devices that provide compression relief to the human spinal column having minimal to no side effect to the overall muscle-skeletal system, few exists.

U.S. Pat. No. 6,036,625 provides a body stretching device for positioning between two sides of a door through its door jamb in closed position. The device extends from its point of attachment on the door jamb to the location of the user's body where the device is worn (i.e. head, shoulders, etc.). The intent is to provide resistant exercise training and muscle development with maximum elastic tension against the sturdiness of a closed door. While the user is able to stretch against the resistant band, the tension force is exerted at an angle against the user's body, particularly between the user's head and the doorjamb. With extensive use over time, the device as claimed in U.S. Patent No. '625 may exacerbate poor posture. The angled tension rearward from the user's head towards the door when in use tugs at the spinal column at an unnatural angle. This causes unintended misalignment and stress to the area around the upper spinal column. The user may overcompensate the rearward tension force to maintain the head in direct vertical position, causing discomfort and unnecessary muscle stress. For purposes of therapeutic spinal decompression and alignment, this device does not allow for passive treatment because the user would have to work to compensate against the awkward positioning of the device.

U.S. patent application Ser. No. 11/402,013 provides a device with more direct vertical alignment on the human spinal column. A planar head plate hangs from a length of support member with projections extending perpendicularly from the lower part of the head plate. The head plate is tied tightly to the user's head with enough strength to hold against the user's body weight. The head plate being strapped to the user's forehead and the projections seated underneath the lower skull near the nape of the user's neck for leverage. This device as provided lacks sturdy support for the wide variety sizes of head sizes. The straps around forehead may easily slip off while the lower protrusions cause unintended pinching of a sensitive area above the neck. The head plate is an impractical device for the intended purpose and is problematic in maintaining a secure comfortable position on the user's head with various tensions applied against it.

U.S. Pat. No. 4,583,532 provides a much more complicated device for creating vertical upward tension against a user's spinal column. As with the prior art described above, this device pulls against the user's head also at an angle. The cushion piece positioned rearward and below the user's skull creates pressure rather than support and resistance against the user's head. Since the head strap is attached to a moving plate, the angle of tension from the strap against the user's head changes as the device rises or lowers along the vertical column. The changing angle of tension against the skull with change of tension in the strap distracts from the desired therapeutic effect and fails to follow a more natural human posture.

U.S. Pat. No. 2,984,236 provides an adjustable head traction device for vertical stretching of a user's spinal column. While the head harness is vertically aligned with the user's spinal column, it provides only a single tension cord. The single tension cord centrally attached to the top end of the head harness, when pulled downward causes the head harness to compress against the head, squeezing the user's skull with increased tension. Pressure around the user's head can unintentionally restrict blood flow, resulting in secondary problems.

There remains a need in the industry for a spinal column stretching aid that follows natural human posture and facilitates healthy spinal, muscular, nervous and arterial alignment in a comfortable self-applying manner.

SUMMARY AND DESCRIPTION OF INVENTION

The invention herein pertains to an improved adjustable spinal traction device for vertical stretching of a user's spinal column. The device comprising a bracket portion, a strap portion and a harness portion. The bracket portion having at least a hook portion and a rod portion. The hook portion having a right angled hook design to fit over the standard edge of a door. The rod portion may comprise one or two metal rods extending away from the hook portion along a horizontal plane and away from a door surface when the hook portion is in use. With both embodiments comprising either one or two rods per hook portion, when in use two rod portions dually extend outward from a door panel. This may be centrally from a single hook, or separately and parallel from their own respective hook. Each rod serves the purpose for allowing the strap portion to be suspended further away from the door surface and with a preferred distance apart, directly over the user's head for a singular lifting affect upward on the user's spine. No other significant tension against the body should be experienced except for the direct lifting of the skull from the spine in a straight manner. The straight lifting effect of this design allows the upper portion of the spine to be lifted in a floating manner to avoid negative side impact from unnatural posture or unnatural constriction, keeping a natural healthy spinal frame structure.

Each rod having two ends, a first end attached to said hook and an opposing second end terminating at their tip (rod tip). The rod tip preferably terminating with nob head and or slanted head to prevent the harness from sliding off. Each rod comprising durable material capable of sustaining constant downward tension of approximately 50 pounds of weight and no less than 5 pounds of weight. Said rod material preferably comprising metal, metal composite or carbon fiber material. When in use, the two rod tips must be spaced apart from the other by a space of at least than 6 inches and preferably between 6 to 8 inches. Spacing of less than 6 inches between rod tips when in use may result in each strap coming too close together at the lower end and pinching the user's head. A space of 6 to 8 inches represents the natural range of head width for an average adult user. When worn, the straps and harness would act more as a cradle against the user's chin as the strap portion pulls directly upward from either sides of the user's head with a lifting and floating affect as opposed to tugging, pulling or pinching at an unnatural or constrictive manner. This is a critical improvement by the fact that the device provides a floating comfort to the user and the only relationship of the device on the body is felt solely by the spine. The intention is to avoid secondary negative impact on the user's body, which is experiencing heightened sensitivity to misalignment.

Those particular brackets having a single hook element with two rods centrally extending therefrom would provide for the ability to adjust spacing between the rod tips by no less than 6 inches. According to this embodiment, the first end of each of the two rods would be rotatingly or swivelly attached to the hook portion, wherein each of the two rods may independently move along a horizontal plane from its central attached position. The angle from their central connection to said hook portion is therefore adjustable. In another embodiment, the first end of each rod having a claw connection piece wrapping around a vertical bar element extending downward from the hook portion such that the two claw connection pieces of each of said two rods overlap each other and swivelly rotate in opposing direction. When rotating each of the two rods centrally around the vertical bar, the overlapping claw connection pieces eventually butt up against the other, preventing further angle expansion or independent rotation of either said rods. The design of the claw connection pieces establishes an automatic maximum angle spread between the two rods to minimize undesirable shifting of the angle spacing between rod tips during use.

Systems comprising brackets with a single rod to a single hook element would involve a composition of two separate units (each unit comprising a single rod extending perpendicularly from a single hook element) wherein the spacing between rod tips would still be between no less than 6 inches and preferably 6 to 8 inches. The two units being positioned in parallel with a preferred distance of separation by 6 to 8 inches. This embodiment may include a bridge between the hook elements to help set the hook ends at an unmovable fixed distance apart. Said bridge may be detachable wherein each hook would be seated thereon at a preferred distance apart. The distance between rod tips according to this embodiment not being adjustable by central angle adjustment as with the swivel type embodiments described above, but rather by distance of separation at the first ends of each rod per unit. The bridge may further comprise a permanent fixed feature to this alternative system and embodiment wherein two rods are permanent attached to a bridge at their first ends at a preferred distance of no less than 6 inches apart, each said rod extending along a horizontal plane parallel to the other and perpendicular to the bridge portion. The bridge portion centrally connected to one or more hook portions. According to the embodiment lacking a bridge, the user would need to manually measure out the distance of space for seating each hook portion of said door's edge such that the space of the two rod tips would reflect the same distance of space. Greater convenience and accuracy of spacing is gained from a bridge element or central swivel capability.

It is important to note that the distance between each rod should be positioned relative to the harness in central position such that the user's head is centrally spaced between said two rod tips and the length of said harness on either sides of the user's head is equal length for purposes of achieving a floating effect upon lift. The main objective of this invention being to provide a lifting effect on the user's spinal column in an even manner and with the user's body being in its natural upright seated posture to avoid unnatural or unintended secondary injury. The tension force and affect should be felt solely along the spinal column of the user. The cumulative affect lifts the user's spine in a neutral floating manner relative to the natural skeletal posture of the body.

Each rod of said two rods (according to any embodiment of the invention herein) preferably extends away from the hook element by a distance of 10 inches. Alternatively speaking, each rod tip should be at least 6 inches away from the vertical door or surface. If each rod is a straight length, then the length of said rod reflects the distance from the door surface. If each rod is nonlinear in shape or is non-perpendicular to the hook end, then the total length of each rod may be greater to achieve a distance away from the door surface of at least 6 inches.

Each rod is connected to a strap portion, said strap portion providing two separate straps. Each rod holds a dedicated strap wherein each said strap is suspended from the rod tip end further away from said door surface. When in use, two straps are suspended parallel to and at equal length with each other by a preferred separation of 6-8 inches apart and at least 6 inches away from the door surface. The length of each strap is preferably adjustable. Each strap may be adjustable along its entire length, along its upper half or lower half. The adjustable portion of the strap is enabled by a strap adjustment mechanism such as a slide through counter tension buckle type element. Preferably, the adjustment portion is located along the lower half of each strap closer to the user reach in seated position. According to this embodiment, the user is able to make continual adjustment during use to obtain a preferred level of tension against his or her body. Hash marks may further be provided along the length of the adjustment portion so that the user may quickly recognize preferred locations for easy quick alignment. Each strap may comprise a portion of elastic material allowing finer change in tension sensed by the body. The elastic portion providing an alternative embodiment to the invention for enhanced tension adjustment.

The tension experienced by the user when the device is applied is a sum total from a combination of features, including the tensile strength of the strap, the length of each strap between each respective rod and the user's head and chin position when worn (the shorter the length the greater the tension), the durability of each rod holding up against each the weight of the user, and the amount of pull exerted by the user's body and head. The device of this invention is intended for passive stretching wherein the weight exerted by the user's body from the head and neck portion results from natural extension against the harness and strap from the user being in a seated position on a chair. Passive stretching in this case meaning minimal movement by the user during use and maintaining a static position under tension. The passive application of this device allows for a slow rehabilitation of the skeletal muscular structure and eventual realignment of the body. This device is not intended or designed for exercises involving frequent repetitive pulling activities, over extension or over exertion of effort that otherwise focus away from passive alignment and more relating to muscle development.

The harness portion of this invention is also carefully designed for comfort and to facilitate ideal alignment of the upper spinal neck area. The harness of this invention comprising the following features: 1) a soft chin rest, 2) a rear head support element, 3) two opposing location of attachment to each said strap. Said soft chin rest comprising a linear piece of material having soft padding for comfort underneath the chin and face to minimize dermal abrasion over extended period of use. Said chin rest preferably long enough to extend between the user's right and left ear lobes. Said length preferably no less than 10 inches and no greater than 18 inches long.

Each end of the chin rest being connected by a rear head strap. The rear head strap comprising a linear piece of soft material, preferably adjustable length by an adjustment mechanism. A first end of said rear head strap connecting to a first end of said chin rest in perpendicular fashion. A second end of said head strap connecting to a second end of said chin rest in perpendicular fashion. When worn, the chin rest would lift against the chin while the head strap lifts and support the rear portion of the head in the same parallel upward direction as the chin rest. Both chin rest and head strap supporting and lifting the front and rear portion head from the same common lifting points with equal effect on the head by said left and right straps. The head strap wrapping around the rear side of the head above the user's ear when worn so as to avoid rubbing against the user's ear.

Importantly, said first end of said chin rest attaches and is coextensive with a first strap and similarly said second end of said chin rest attaches and is coextensive with a second strap such that, when used, said first and second strap lifting said chin rest against the user's chin in upward parallel manner at least 6 inches apart from each other. The parallel direct upward lifting force of each of the two straps creates an even and equal tension against the user's spine from the left and right side of the user's head. Unlike the prior art where the straps centrally connect, causing a pinching and pulling affect, the spread of tension between the left and right side of the user's head in this case results in a lifting affect. By lifting, rather than pinching and pulling of the user's head and neck away from the spine, unnecessary tension to muscles at the base of the head and neck area is minimized or avoided. When the body is stretched and pulled by the pinching affect, muscles at the base of the neck will contract and be stressed against the concentrated central force, resulting in unnatural skeletal muscular compensation to the event. When extended by lifting affect, the force is spread further apart resulting in a more natural adjustment to the upper skeletal muscular and with minimized contraction compensation affect. The body's upper skeletal muscle relationship is maintained in a more natural and less stressed condition while the spine is decompressed by the extension exercise.

The method of rehabilitation and decompression of a human spinal column comprising the device described above worn by an individual in seating position. The device first being hooked to the top of a door jam or floating wall where the rod elements are spaced approximately 6-8 inches apart at their rod tips ends. Said first and second strap of said harness attached toward the rod tip ends of said first and second rod element. The head strap of said harness being positioned most proximate to the door or floating wall surface while said chin strap portion facing outward therefrom. A chair being positioned centrally underneath said device with equal spacing between said first and second rod tips. While in standing position, said chin rest positioned underneath the chin of the user's head and said head strap positioned rearward of said user's head. Said head strap tightened to comfort. Said individual proceeds to sit down on said chair, reaching upward to said first and second strap, adjusting each strap to preferred level of comfort and lift. Alternatively, said straps may be adjusted to a predetermined length according to a suggested location based on hash mark indications. Once the user is in seated position and the device properly worn and adjusted, the user would stay in position for approximately 15-20 minutes of stretching. The user should practice approximately 15-20 minutes of this therapy on a daily basis. Regular daily short term stretching by this device and method provides longer term decompression and relaxation of pinched nerve endings, allowing the user to regain feel in extremities such as fingers, arms and legs. This device helps to extend or avoid the need for spinal surgery, with great relevance to those who suffer from chronic back pain and bulging or herniated discs. The device is compact, portable and lightweight and therefore allows the user to continue this therapy anywhere at any convenient or comfortable time.

Other features, advantages, and object of the present invention will become more apparent and be more readily understood from the following detailed description, which should be read in conjunction with the accompanying drawings.

DETAILED DESCRIPTION OF THE INVENTION

Figure 1:
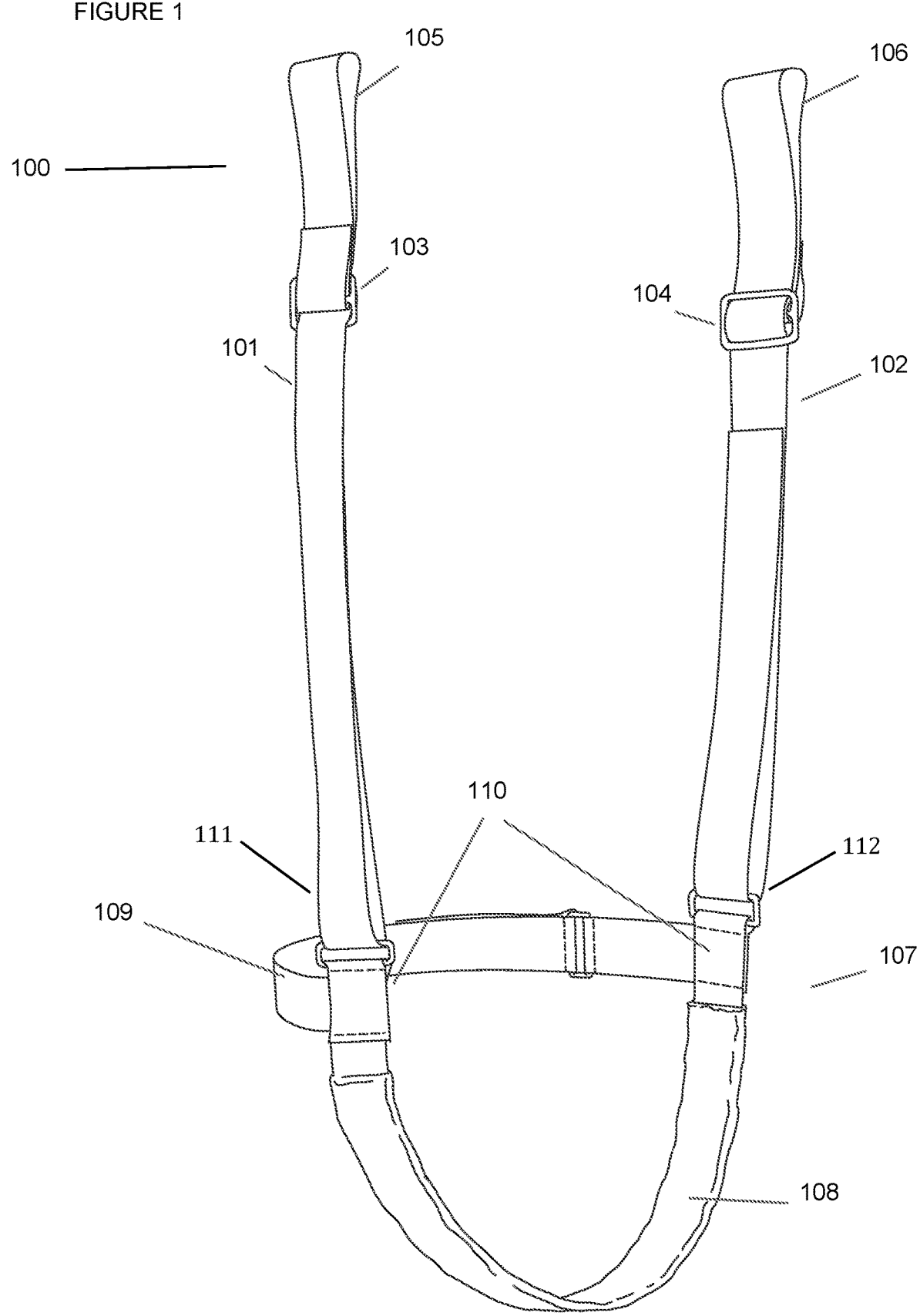
FIG. 1 presents a perspective view of a preferred embodiment of the harness portion of the device.
Figure 2:
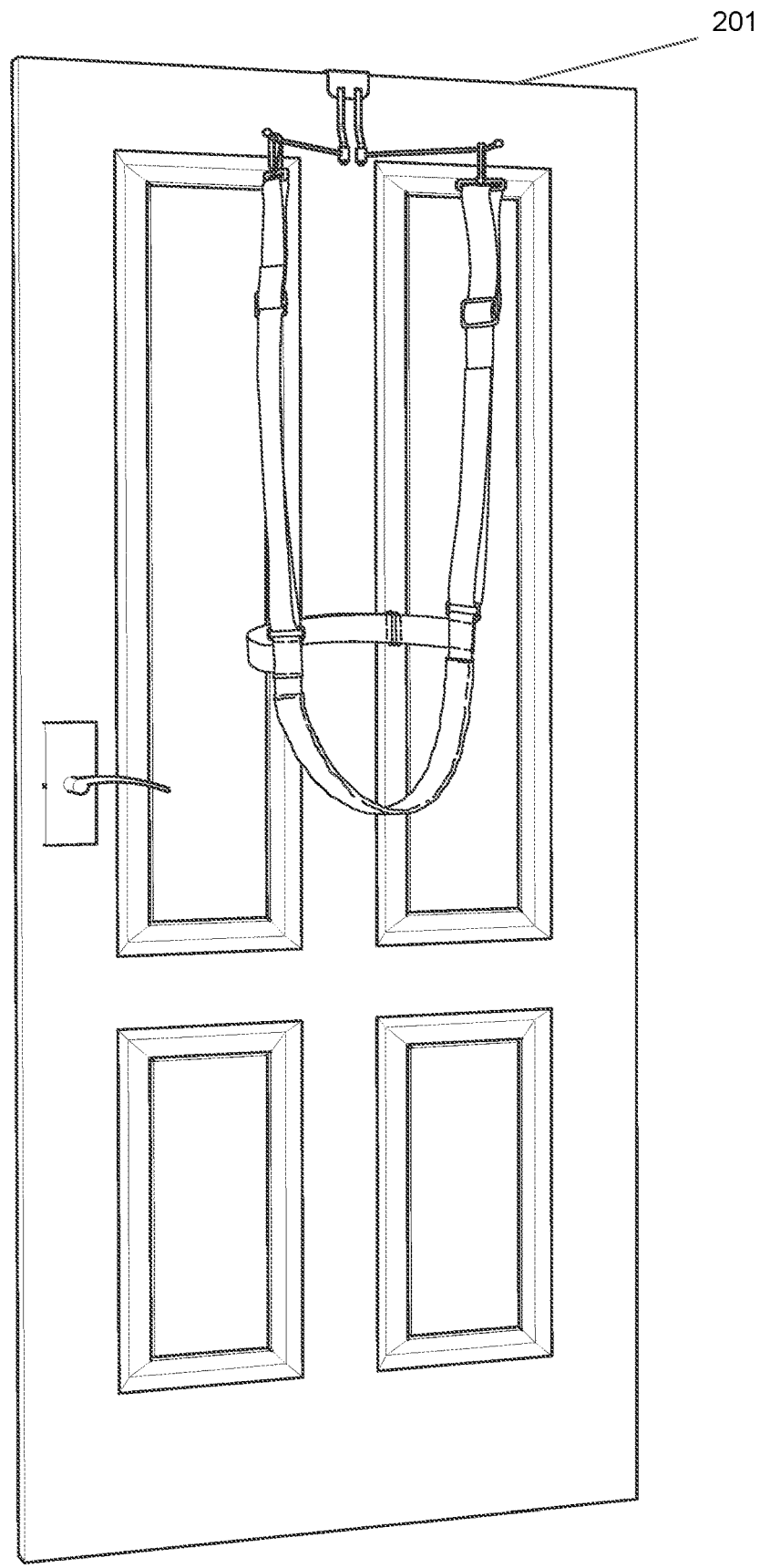
FIG. 2 presents a perspective view of an alternative embodiment of the device.

FIG. 1 provides an example of a preferred embodiment of the harness portion 100 of the device. The harness portion comprising two lengths of straps 101,102 with an adjustable means 103.104. The means for adjusting length 103,104 may be known technology in the art, comprising but not limited to sleeve through buckles, buttons, or hook and loop components. The length of each strap (of said first and second strap) should be long enough to extend from the top edge of a door 201 down, 311 towards the head of a person in seated position adjacent to said door to achieve the purpose of this invention (See FIGS. 2 and 3). Each said strap 101,102 having a top end 105,106 loosely connectable to the bracket portion device. The ability to loosely and removably connect to the bracket portion of the device is to enable the entire device to be broken down and taken a part for portability. The detachably connectable element may simply be a hook or sleeve feature that slides over or around each rod extending from the bracket portion. Each strap may comprise elastic material in part or in total.

Figure 3:
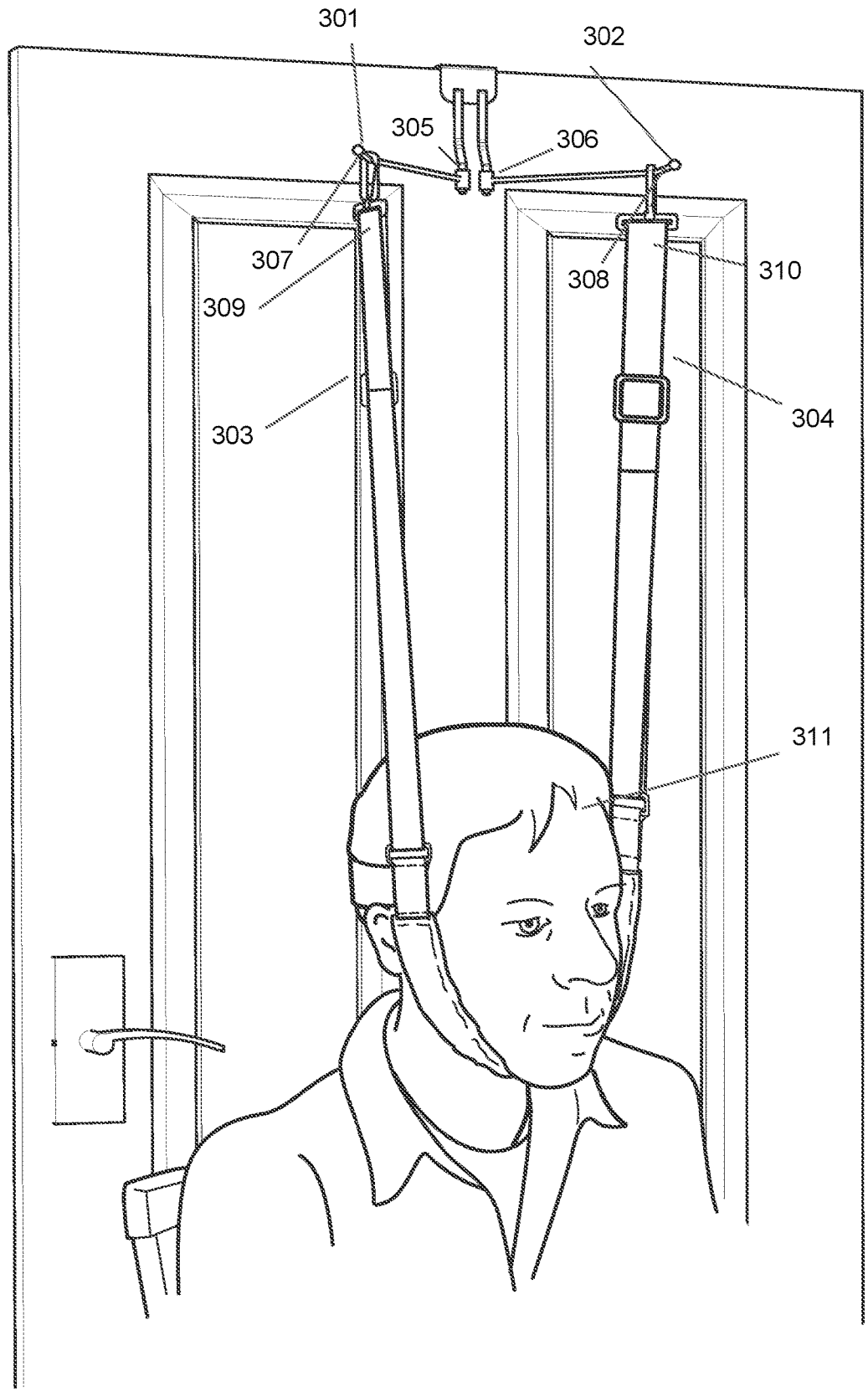
FIG. 3 presents a perspective view of an alternative embodiment of the device in use.

The harness portion further comprising a head strap 107. The head strap comprising a chin rest 108 and an adjustable rear head strap 109. The chin rest 108 is coextensive between the first strap 101 and second strap 102 to create a long linear piece of material wherein the chin rest 108 is centrally positioned. The adjustable rear head strap 109 connects as a bridge between the first strap 101 and second strap 102, at either bottom end 111, 112 connection to said chin rest 109. This point of connection between the three elements is preferably a 90 degree connection 110 relative to said adjustable rear head strap. When worn, as illustrated in FIG. 3, the location of connection would be located above the user's ear to avoid discomfort from the competing pressures against the ear itself. The three elements of the harness portion at their point of connection 110 is a location where competing forces converge and can be felt on the side of the user's head. By placing that point of pressure above the user's ear and directing the force upward and to the side of the user's head, the effect such as a pinching effect would not be experienced by the user. The harness 100 may also comprise elastic material in part or in total.

When in use, as illustrated in FIG. 3, each of the two rods tips 301, 302 are spread apart by a distance of 6 to 8 inches, which directs the spread of the straps 303,304 by that same distance. The first end of each rod 305,306 is preferably adjustable by swivel manner such that the user may easily maintain a constant parallel position of the two straps 303,304 to the side of his or her head with slight changes of head position during use. The rod tips 301,302 extend beyond the surface of the door by at least 6 inches to allow the first and second strap 303,304 to hang directly over either side of the user's head according to their natural sitting posture. The rod tips 301,302 of each rod also having a knob ending or an upward slant 307,308 to prevent the top end of each strap 309,310 from easily being pulled off. Further, the overall bracket portion comprising durable material that can sustain the downward weight or force of the user's upper body against the tension of the first and second straps. This may be greater as great as 50 pounds and no less than 5 pounds of downward force against each and both rods.

Figure 4:
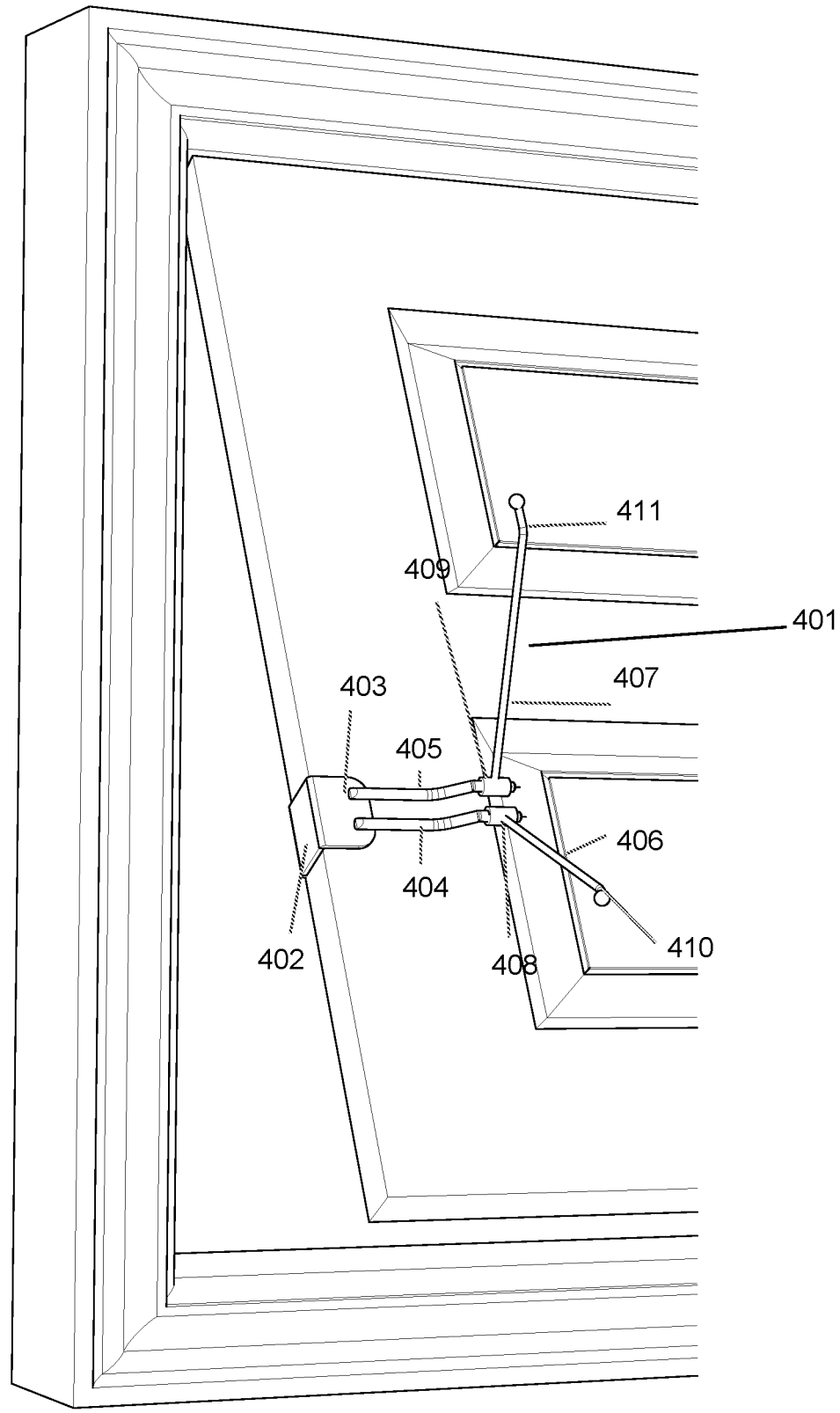
FIG. 4 presents a perspective view of an embodiment of the bracket portion of the device.
Figure 5:
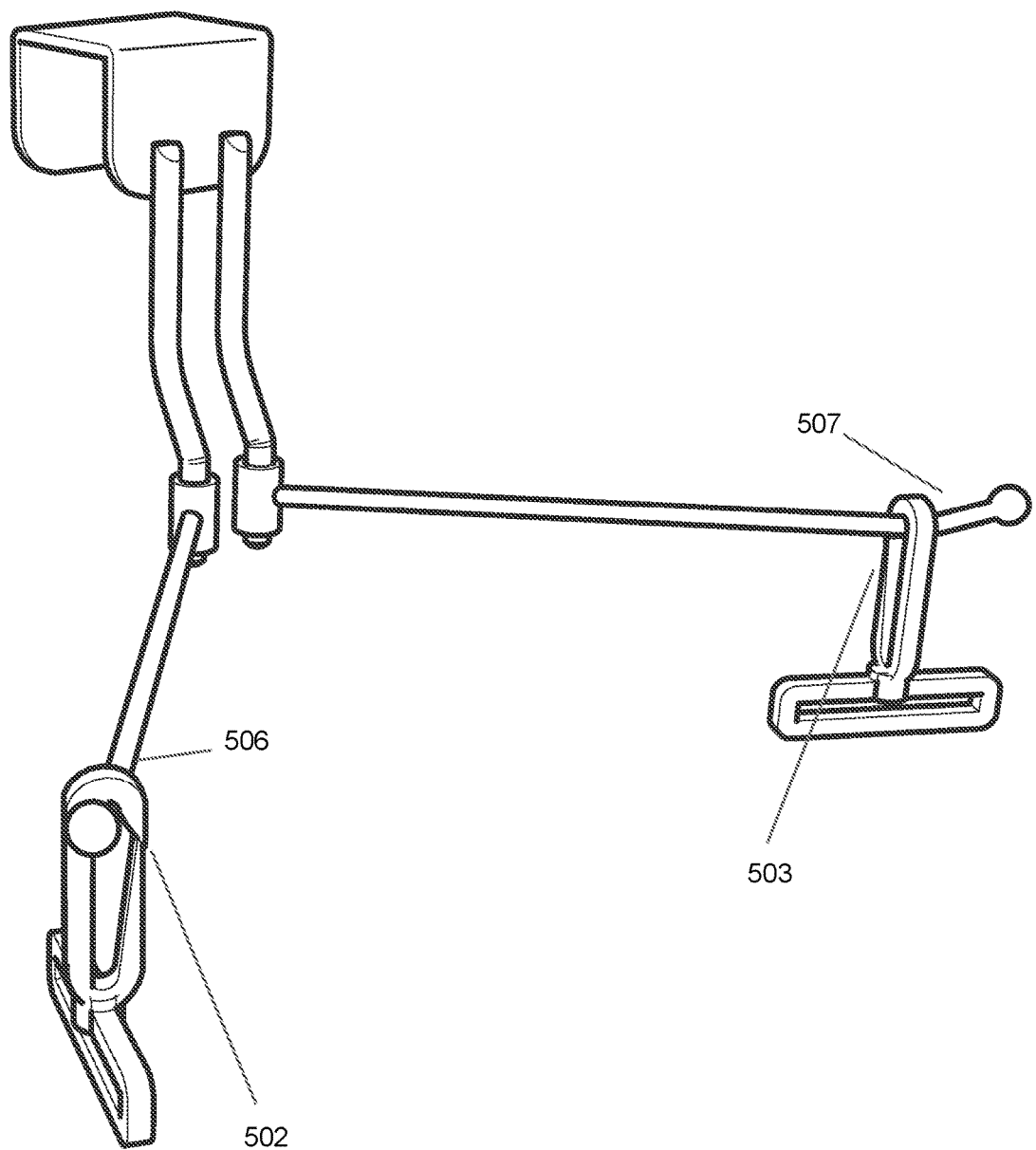
FIG. 5 presents a perspective view of an embodiment of the bracket portion of the device.

FIG. 4 provides illustration of a preferred embodiment of the bracket portion 401 comprising a hook feature 402, a bridge feature 403 coextensive with said hook feature 402, two vertical bars extending 404,405 from said hook feature 402 separated by a preferred distance, and two rod features 406,407 each having a first end swivelly 408,409 attached to each individual vertical bar 404,405 and a second end with a rod tip 410,411. FIG. 5 provides a second perspective view of the same embodiment described in FIG. 4 illustrating a detachably connectable element 502,503 of each first and second strap removably hooked onto or sleeved over each said rod tip 506,507.

Figure 6:
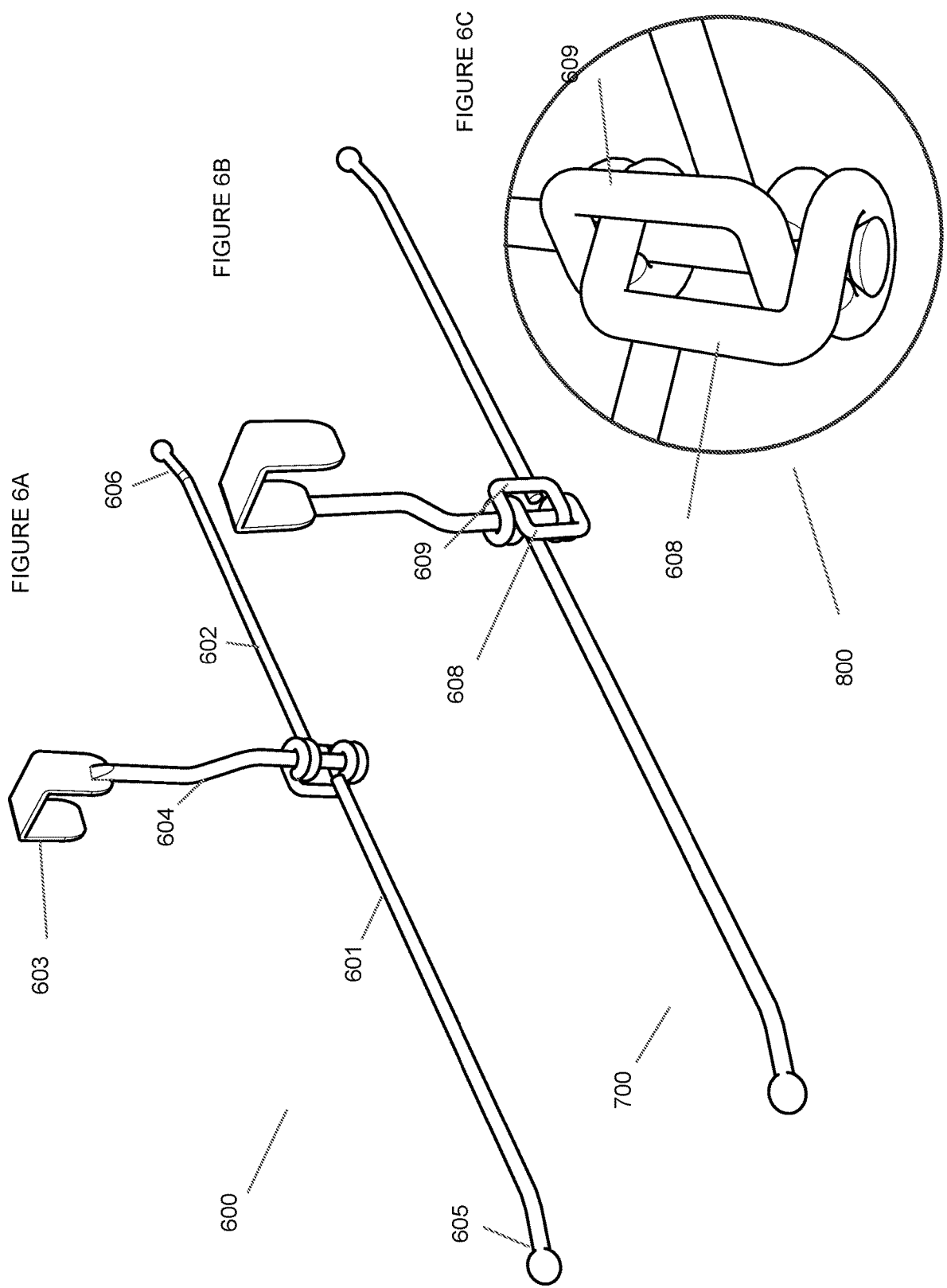
FIGS. 6A and 6B presents a perspective view of an alternative embodiment of the bracket portion of the device.
FIG. 6C presents an exploded view of a portion of the alternative embodiment presented in FIGS. 6A and 6B.

FIGS. 6a, b and c provides a front 600, rear 700 and exploded 800 view illustration of an alternative embodiment of the bracket portion 600 of this invention. This embodiment provides for two rods 601,602 attached to the hook 603 element at a single vertical bar 604 and without a bridge feature. The distance between a first rod tip 605 and second rod tip 606 is determined and adjusted at their first rod ends 607 which are swivelly connected to the single vertical bar 604 and hook portion 603. This embodiment of the bracket portion 600 provides a new method of interconnecting the first ends 607 of each said first and second rod pieces 601,602. The alternating interconnection of claw like feature 608,609 at the first end of said first rod 601 and second rod 602 results in their abutment when swiveled in opposite directions. The location of abutment 610 determines the maximum angle of opposing rotation. As such, the claw feature 608,609 and design may be manipulated such that the maximum angle of spread between the first and second rod 601,602 at their respective first ends 607 may automatically stop at a preferred spot 610 and establish the desired 6 to 8 inch spread at their opposing rod tip ends. This results in the improved feature of this invention which provides guidance to the user of the desired distance of spread to facilitate the floating lift effect of the device on the user during use.

Figure 7:
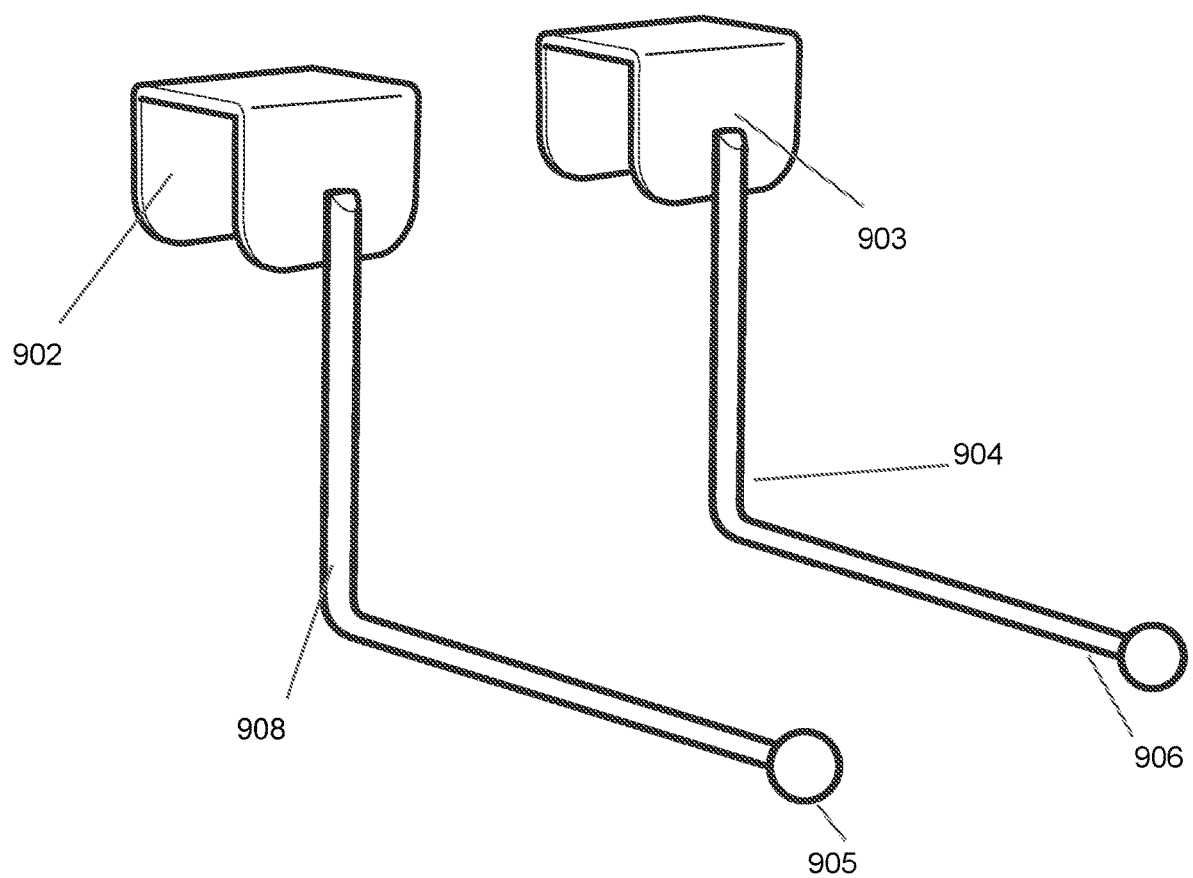
FIG. 7 presents a perspective view of an alternative embodiment of the bracket portion of the device.

FIG. 7 provides for yet another embodiment of this invention comprising two hook portions 902,903, each hook portion 902,903 attached to a separate individual rod 908, 904 feature in fused manner. The distance between each rod tip 905,906 is directly proportional and relative to the position of the hook portion 902,903 over the door. This alternative embodiment allows automatic adjustment of desired spacing between the two rod tip ends 905,906 but is not as convenient as the above described embodiments of FIG. 5 and FIG. 6. This embodiment does provide improvement from the prior art in that a spread of at least 6 to 8 inches is achievable to enable the floating lift effect of this invention.

Having fully described at least one embodiment of the present invention, other equivalent or alternative devices will be apparent to those skilled in the art. The invention has been described by way of summary, detailed description and illustration. The specific embodiments disclosed in the above drawings are not intended to be limiting.

I claim the following invention:

1. A spinal traction device comprising:

a bracket portion, a strap portion, and a harness portion, said bracket portion comprising a hook element and a pair of rod elements, said hook element comprising a at least one or more hook components, each hook component of said one or more hook components attached to at least one vertical bar such that when said hook component is suspended over a vertical panel, two vertical bar elements extend vertically downward in adjacent parallel manner to form two parallel vertical bars, said hook element having a first end comprising said at least one or more hook components and a second end comprising a distal end of each vertical bar of said two parallel vertical bars, said distal end of each vertical bar of said two parallel vertical bars is removably connectable to a rod element of said pair of rod elements in perpendicular and swivel manner, a horizontal distance of space between the farthest ends of said pair of rod elements is adjustable by swivel adjustment by at least 6 inches or greater there between, each said rod element of said pair of rod elements having a linear, curved, or angled shape, or combinations thereof, said strap portion comprising a first strap and a second strap, each said first and second strap having a top end and a bottom end, said top end of each said first and second strap is removably attachable to and suspendable from each said rod element of said pair of rod elements, each said first and second strap having a length that is adjustable, each said first and second adjustable straps comprises a length of up to five feet, said harness portion comprising a chin strap and an adjustable rear head strap, said chin rest comprising a length of, said chin strap having a first end and a second end wherein said first end of said chin strap is attachable to said bottom end of said first strap, said second end of said chin strap is attachable to said bottom end of said second strap, said adjustable rear head strap comprising a length of flexible material with a first end and a second end that is adjustable in length, said first end of said adjustable rear head strap is perpendicularly connectable to said bottom end of said first strap, said second end of said adjustable rear head strap is perpendicularly connected to said bottom end of said second strap.

2. A self-administrating spinal traction therapy system comprising a spinal traction device according to claim 1 wherein said spinal traction device is wearable by a user, lifting the user's spine in direct upwardly manner while said user is seated an upright position adjacent to a door, said hook element of said device is suspendable over a top edge of said door, said rod elements extend away from a door surface by at least 6 inches said pair of rod elements each attachable to a first or second strap, and said pair of rod elements are swivelly adjustable relative to each other such that each said strap of said first and second straps are disposed at least 6 inches away from the door surface in suspended manner and the distance between said first and second strap are each adjustable by swivel movement of said pair of rod elements to maintain a continual centralized position between said first and second straps and a continual parallel position of said first and second straps relative to said door surface.

* * * * *